US00PP24659P3

(12) United States Plant Patent
Coiner

(10) Patent No.: US PP24,659 P3
(45) Date of Patent: Jul. 22, 2014

(54) FLORIBUNDA ROSE PLANT NAMED 'PAT'S PINK'

(50) Latin Name: *Rosa hybrida*
Varietal Denomination: Pat's Pink

(76) Inventor: James W. Coiner, Covina, CA (US)

( * ) Notice: Subject to any disclaimer, the term of this patent is extended or adjusted under 35 U.S.C. 154(b) by 38 days.

(21) Appl. No.: 13/573,336

(22) Filed: Sep. 10, 2012

(65) Prior Publication Data

US 2014/0075615 P1 Mar. 13, 2014

(51) Int. Cl.
*A01H 5/00* (2006.01)

(52) U.S. Cl.
USPC ..... Plt./149

(58) Field of Classification Search
USPC ..... Plt./149
See application file for complete search history.

*Primary Examiner* — Annette Para
(74) *Attorney, Agent, or Firm* — Christie, Parker & Hale, LLP

(57) ABSTRACT

A new variety of Floribunda rose suitable for garden decoration, having flowers of pink coloration.

1 Drawing Sheet

Classification: The present invention relates to a new *Rosa hybrida* plant.

Variety denomination: The new plant has the varietal denomination 'PAT'S PINK'.

BACKGROUND OF THE INVENTION

This invention relates to a new and distinct variety of Floribunda Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant has a bushy compact growth habit, suitable for outdoor garden decoration. The plant is fairly disease resistant.

Asexual reproduction of the new variety by budding as performed in Kern County shows that the foregoing and other distinguishing characteristics come true to form and are established and transmitted through succeeding asexual propagations. 'Pat's Pink' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Sexy Rexy' (U.S. Plant Pat. No. 6,713) by the following combination of characteristics: a darker, more iridescent pink, on a sturdy vigorus plant.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly, sometimes usually in clusters of two to three per stem. Flowers are may be borne in regular to flat clusters on strong medium to long stems (about 24 cm to about 45 cm). Outdoors, the plant blooms abundantly and continuously during the growing season. The flowers have a very slight fragrance.

BUD

The peduncle is about 3.2 cm to about 5.2 cm in length, of average caliper, and erect. It is usually smooth, with many numerous stipitate glands, and many numerous hairs and prickles. Peduncle color is near between 142c and 141d.

Before the calyx breaks, the bud is about 1.5 cm to about 2 cm in diameter at the widest point, about 2.5 cm to about 3 cm in length, and ovoid in shape with a conspicuous neck. The surface of the bud bears some foliaceous appendages tomentum stipitate glands and glandular bloom, usually with slender bristle-like foliaceous parts extending beyond the tip of the bud about one fourth or more of its length. Bud color is near between 138a and 144a.

The sepals are about 4 cm to about 5 cm in length and about 2 cm to about 2.5 cm in width at the widest point. The outer surface color of the sepal is near between 144a and 147c. The inner surface color of the sepal is near between 143c and 139d and covered with fine wooly tomentum; sepal margins are lined with stipitate glands and hairs.

As the petals open (after the calyx breaks), the bud is about 2 cm to about 3 cm in diameter at the widest point, about 3 cm to about 4.5 cm in length, and ovoid in form.

The color outside of the opened petal is between 74b and 74c.

The color inside the petal is close to 74b.

BLOOM

When fully open, the bloom ranges from about 9 cm to about 10 cm in diameter. Petalage is semi-double with about 18 to 25 petals and about 3 to 5 petaloids irregularly arranged. When partially open, the bloom form is cupped, and the petals are somewhat spiraled with petal edges very moderately somewhat rolled outward. When fully open, the bloom form is somewhat very moderately flat to cupped, and the petals are loosely imbricated with petal edges very moderately rolled outward.

PETALS

The substance of the petals is medium and of average thickness, with upper surfaces slightly shiny to velvety and under surfaces slightly shiny to velvety also. The petals are about 4 cm to about 4.5 cm in length and about 5 cm to about 5.5 cm in width at the widest point. Petal margins are serrate.

The outer petals are oval to ovate to obovate in shape with apexes somewhat rounded and sometimes usually slightly notched with one to two or more notches.

The inner petals are are oval to ovate to obovate in shape with apexes somewhat rounded and sometimes usually slightly notched with one to two or more notches.

Petaloids are about 1 cm to about 2 cm in length and about 3 cm to about 4 cm in width at the widest point. Petaloids are shaped round to oval with with flat apices.

NEWLY OPENED FLOWER

The upper surface color of the outer petals is near between 74b and 74c.

The under and upper surface color of the intermediate petals is near between 74c and 74d.

The upper surface color of the inner petals is near between 74c and 74d.

The under and upper surface color of the petaloids are similar in coloration to the upper and under surfaces of the intermediate and inner petals.

The general tonality of the newly opened flower is near between 74b and 74c.

THREE-DAY OLD FLOWER

The outside surface of the outer and inner petals is between 74b and 74c with a moderately small splash of 186d at the base.

The inside surface of the outer and inner petals is between 74c and 74d with a moderately small splash of 186d at the base.

The general tonality of the three day old flower is near 74c.

In October, in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average to many in number (average about 85) and are arranged regularly about the pistils. The filaments are of very moderately medium to long length (about 6 mm to about 14 mm) most with anthers. Filaments are near between 12c and 12d in color. The anthers are very moderately somewhat small to medium to large for the class and all open approximately at the same time. Anther color is near 26a when immature and near 172a at maturity. Pollen is somewhat sparse and near 15c in color.

FEMALE REPRODUCTIVE ORGANS

Pistils vary in number (average about 90). The styles somewhat uneven, moderately short in length, average in caliper, and moderately bunched. Stigma color is near 10d. Style color is near 42c. Ovaries are usually enclosed in the calyx.

Hips are not apparent on this variety when grown in Wasco, Calif.

FOILAGE

The compound leaves are usually comprised of three to five leaflets and are borne to normal quantities. The five-leaflet leaves are about 3.5 cm to about 7 cm in length and about 2 cm to about 4 cm in width at the widest point, leathery in texture, matte in finish. The terminal leaflets are about 4 cm to about 7.5 cm in length and about 3 cm to about 6 cm in width at the widest point, shaped moderately oblong to obovoid with somewhat acute to apexes and round bases. Their margin is usually serrate.

The upper surface color of the mature leaf is near 141a and the under surface color of the mature leaf is near 138b. The upper surface color of the young leaf is near 134b. The under surface color of the young leaf is near 134d.

The rachis is average in caliper and moderately rough. The upper side is shallowly grooved with few hairs and stipitate glands and prickles on the edges of the grooves. The under side of the rachis is smooth with few hairs and stipitate glands and somewhat moderately small prickles. The rachis color is near 137c.

The stipules are about 20 mm. in length and somewhat narrow to medium width (about 8 mm to about 12 mm) with points that usually turn out at an angle of 45 degrees toward the stem. The stipules color is near 137c.

The petiole is average in caliper and rough. The upper side is moderately grooved with few hairs and stipate glands. The under side of the rachis is somewhat rough with few hairs and stiptate glands and small prickles. The petiole is about 5 cm to 6 cm in length and about 5 cm to 6 cm in diameter at the widest point. The petiole color is near 164c.

The plant displays an average to above average degree of resistance to powdery mildew and rust as compared to other commercial varieties grown under comparable conditions in Wasco, Calif. The plant's winter hardiness and drought/heat tolerance are yet to be determined.

GROWTH

The plant has a bushy compact growth habit (about 100 cm to about 120 cm in height and about 80 cm to about 90 cm spread at the widest point), with very full branching. It displays vigorous growth and the canes are of medium caliper for the class.

The color of the major stems is near 141d. They bear several large prickles that are about 8 cm to about 10 cm in length. The large prickles are hooked downward with a medium length rounded base; prickle color is near 183a.

The color of the branches is near between 144a and 138b. They bear few prickles which are of similar size and shape to the large prickles on the major stems; prickle color is near 183b. The branches bear few small prickles of similar shape and coloration and which are near 183c.

The color of the new shoots is near between 45b and 45d. They bear few prickles which are of similar size and shape to the large prickles on the major stems; prickle color is near between 144a and 138b. The shoots bear few prickles of similar shape and coloration and which are near between 183c and 175b in color.

I claim:

1. A new and distinct Floribunda rose plant of the variety substantially as described and illustrated herein.

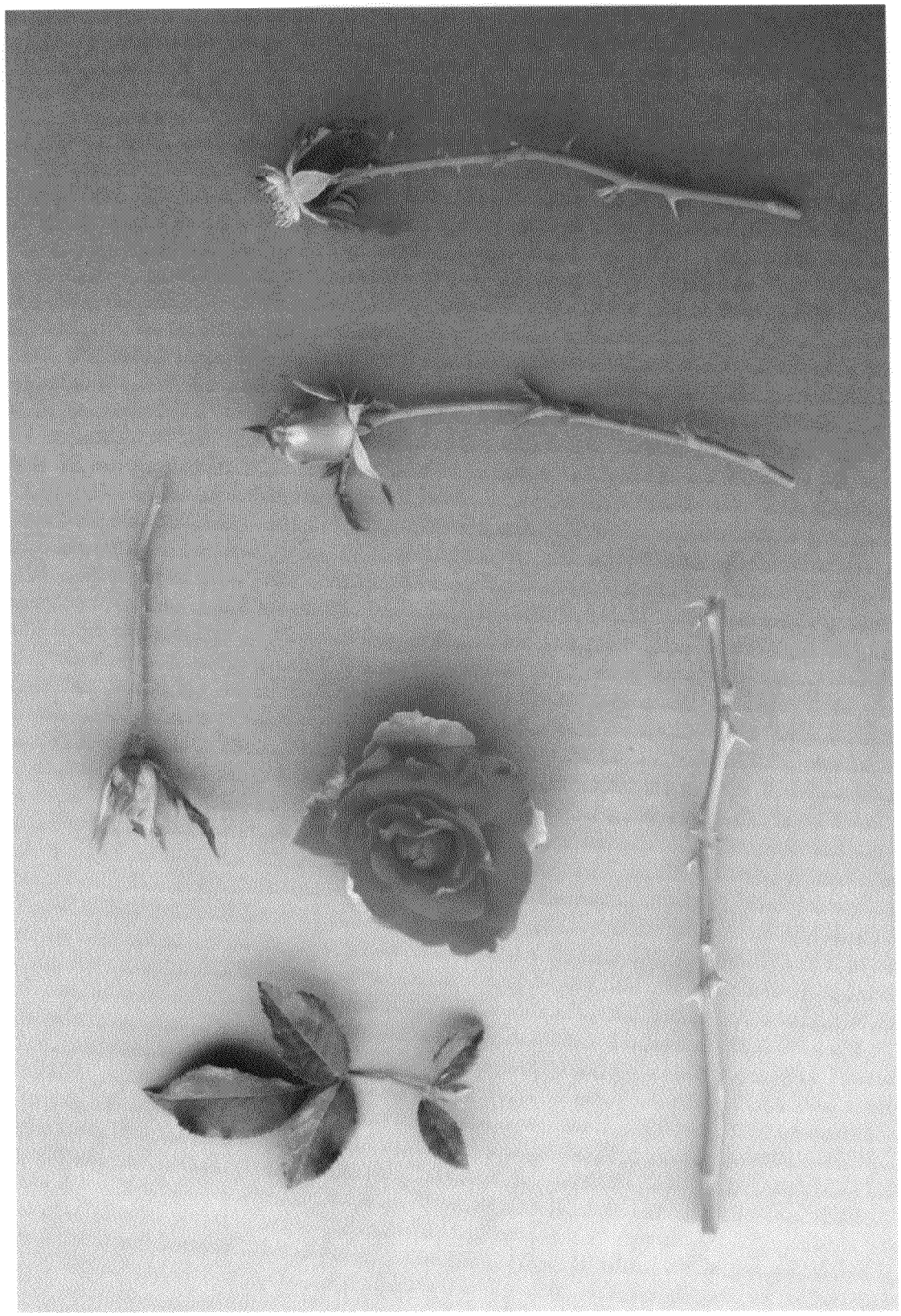

* * * * *